United States Patent [19]

Colaruotolo et al.

[11] Patent Number: 4,511,657
[45] Date of Patent: * Apr. 16, 1985

[54] TREATMENT OF OBNOXIOUS CHEMICAL WASTES

[75] Inventors: Joseph F. Colaruotolo, Grand Island, N.Y.; Robert L. Irvine, Mishawaka; Lloyd H. Ketchum, Jr., South Bend, both of Ind.; Wei-chi Ying, Grand Island, N.Y.

[73] Assignee: Occidental Chemical Corporation, Niagara Falls, N.Y.

[*] Notice: The portion of the term of this patent subsequent to Oct. 16, 2001 has been disclaimed.

[21] Appl. No.: 381,866

[22] Filed: May 25, 1982

[51] Int. Cl.³ .................... C12N 1/22; C12N 1/36; C12R 1/38; C12K 1/02
[52] U.S. Cl. .................... 435/253; 435/245; 435/262; 435/874; 210/611; 935/59
[58] Field of Search .............. 435/245, 262, 281, 874, 435/253, 172.1, 172.3; 210/610, 611

[56] References Cited

U.S. PATENT DOCUMENTS

| 3,660,278 | 5/1972 | Mimura et al. | 210/611 |
| 3,779,866 | 12/1973 | Azarowicz | 435/281 |
| 3,923,603 | 12/1975 | Chakrabarty et al. | 435/874 |
| 3,979,383 | 9/1976 | Prudom | 435/281 |
| 4,169,049 | 9/1979 | Salkinoja-Salonen | 210/909 |
| 4,352,886 | 10/1982 | Pillis et al. | 435/262 |
| 4,391,887 | 7/1983 | Baumgarten et al. | 210/611 |
| 4,401,569 | 8/1983 | Jhaveri et al. | 210/610 |
| 4,447,541 | 5/1984 | Peterson | 435/874 |
| 4,452,894 | 6/1984 | Olsen et al. | 435/253 |
| 4,477,570 | 10/1984 | Colaruotolo et al. | 435/253 |

FOREIGN PATENT DOCUMENTS

| 1277632 | 6/1972 | United Kingdom | 210/611 |
| 0647339 | 2/1979 | U.S.S.R. | 435/281 |

OTHER PUBLICATIONS

Yagi et al, "Degradation of Polychlorinated Biphenyls by Microorganisms", Journal W.P.C.F., 52(5), pp. 1035–1043, (1980).

Liu, Bull. Environ. Contam. Toxicol., 29(2), pp. 200–207, (1982)—Chem. Abst. 97:132856w.
Liu, Bull. Environ. Contam. Toxicol., 27(5), pp. 695–703, (1981)—Chem. Abst. 96:40312s.
Kobabayashi et al., "Microbial Removal of Hazardous Organic Compounds", Environmental Science and Technology, 16(3), (1982), pp. 170A–183A.
Patterson et al., "Biodegradation of Hazardous Organic Pollutants", CEP, (Apr. 1981), pp. 48–55.
Vandenbergh et al., "Isolation and Genetic Characterization of Bacteria That Degrade Chloroaromatic Compounds", Applied and Environmental Microbiology, 42(4), (1981), pp. 737–739.
Omori et al., "Bacterial Dehalogenation of Halogenated Alkanes and Fatty Acids", Applied and Environmental Microbiology, 35(5), (1978), pp. 967–971.
Irvine et al., "Sequencing Batch Biological Reactors-An Overview", Journal of Water Pollution Control Federation, 51(2), (1979), pp. 235–243.
Richardson et al., "A New Treatment for Biodegradable Waste", Proc. Int. Water Conf. Eng. Soc. West. Pa. 40th, (1979), pp. 281–284. (Abstract).
Kellogg et al., "Plasmid Assisted Molecular Breeding: New Technique for Enhanced Biodegradation of Persistent Toxic Chemicals", Science 214, (12-1981), pp. 1133–1135.
Dorn et al., "Isolation and Characterization of a 3--Chlorobenzoate Degrading Psuedomonad", Archives of Microbiology 99, (1974), pp. 61–70.

Primary Examiner—Thomas G. Wiseman
Assistant Examiner—John E. Tarcza
Attorney, Agent, or Firm—J. F. Tao; P. F. Casella; W. G. Gosz

[57] ABSTRACT

This invention relates to the treatment of obnoxious waste effluents, both industrial and municipal, such as chemical waste landfill leachates, chemical process wastewaters and other obnoxious waste effluents by the use of microbial cultures, especially adapted to biodegrade the obnoxious chemicals in the chemical wastes, such as activated sludge and inoculants for activated sludge, and the new inoculated activated sludges and their use in biological wastewater systems such as continuous and batch reactors.

16 Claims, No Drawings

TREATMENT OF OBNOXIOUS CHEMICAL WASTES

BACKGROUND OF INVENTION

Since World War II the chemical industry has grown to the point where there are over 35 million metric tons of obnoxious or hazardous wastes being generated. Large quantities of these wastes contain synthetic halogenated materials such as found in dielectric fluids, flame retardants, refrigerants, heat transfer fluids, lubricants, protective coatings, pesticides, including herbicides and insecticides. Furthermore, it is well knon that both the petroleum industry and the coal industry contribute many more millions of metric tons of hazardous chemical wastes to be disposed of which contain obnoxious organic compounds. Many of these materials are non biodegradable or recalcitrant, i.e. difficult to biodegrade.

In many cases, these materials and the by-products or residues from their manufacture have been accumulated in landfills or discharged (treated or partially treated) into the conduits of municipal sewer systems. In the case of landfills and over the course of time, and by a process of liquifaction the contents of the landfill ultimately produces a leachate which must be disposed of.

In the case of disposing of chemical waste effluents into the municipal systems, the chemical waste effluents are mixed and diluted into the municipal wastes and they become contaminants which are difficult or impossible for the municipal wastewater treatment plants to handle in a way which meets the standards of disposal of such effluents and the sludges produced, set up by the Federal and State governments. In some cases the toxic chemicals pass thru the municipal wastewater treatment system and show up "untreated" in the waste sludge and waste effluents.

All kinds of methods and techniques have been proposed and used for disposing of and/or treating these chemical wastes and their byproducts to make them compatible with the environment. In spite of all the effort and money being spent, no technology has evolved which is economically and technically satisfactory.

BRIEF DESCRIPTION OF THE INVENTION

This invention relates to methods, materials and systems for treating obnoxious or hazardous waste effluents containing halogenated organic compounds to render them more compatible with the ecosphere in a way which protects the environment and water supplies of the general population. More particularly, this invention relates to the method of treating chemical process wastewaters and chemical waste landfill leachates containing recalcitrant organic compounds, by a process which comprises treating leachates with activated sludge containing bacteria capable of metabolizing the obnoxious organics.

Still further, the invention relates to improving the ability of activated sludge to metabolize recalcitrant organics by the process comprising:

1. Analyzing the chemical waste to determine the composition of the contaminants to be removed.
2. Preparing a culture of a microbial organism capable of metabolizing the recalcitrant contaminants.
3. Inoculating a biologically active waste treatment sludge capable of metabolizing the non-recalcitrant components of the chemical wastewater or leachate with the prepared culture of the microorganisms obtained by Step 2.
4. Employing the organism system obtained by Step 3 in a biological wastewater facility to biodegrade the recalcitrant and non-calcitrant chemical components of the chemical process wastewater or leachate.
5. Disposing of the waste effluent and waste sludge produced.

Still further, we found, much to our surprise that when employing inoculants containing strains of bacteria that have been continuously exposed to the high concentrations of contaminants in long established chemical landfills containing obnoxious halogenated organic chemicals, that such strains when inoculated into the mixed cultures of the activated sludge not only survive but actually eventually dominate the population in the mixed culture. This is true of the *Pseudomonas cepacia* var., *niagarous,* as will be exemplified hereinafter, which were prepared in accordance with the teaching of copending application Ser. No. 06/305 079 filed Sept. 24, 1981 of which one of the coinventors of the present application is also a coinventor in that application.

This invention also provides new compositions of matter which are combinations of activated sludge and new microbial materials which compositions are useful in the degradation of both municipal and industrial waste effluents containing recalcitrant halo-organic chemicals.

THE PRIOR ART

An overview and assessment of biological treatment systems relative to their overall applicability to industrial processing waste streams which discusses the various processes which may be considered including enzyme treatment, activated sludge, trickling filter, aerated lagoon, waste stabilization pond, anaerobic digestion and composting was prepared by Sandra L. Johnson and published in Unit Operations for Treatment of Hazardous Wastes (1978) pages 168 thru 217 published by Noyes Data Corporation.

The present state-of-the-art for treating chemical landfill leachates involves employing a complicated series of process steps which are uneconomical, time consuming, and difficult to manage and operate with results that meet the stringent effluent restrictions imposed by Federal and State law. See for example McDougall, W. J., Fusco, R. A. and O'Brien, R. P., "Containment and Treatment of the Love Canal Landfill Leachate" in Journal of Water Pollution Control Federation Vol. 52, pgs. 2914–2924 (1980). This and similar state-of-the-art techniques for disposing of chemical landfill leachates are expensive, inefficient and leave room for improvement.

In so far as municipal wastewater treatment systems handling of effluents containing chemical wastes have been conduited into the sewerage system are concerned, many complex treatments have also become necessary and in most cases ineffective in being able to handle sewerage wastes from chemical plants, oil refineries, shale oil wastes, wastes from meat packing plants among other industry effluents with the result that many municipal systems disposing of these effluents are sustaining conditions in the environment which do not contribute to the improvement of the environment.

A recent development in the treatment of wastewater designated as Sequencing Batch Biological Reactors (SBR) is reported by Robert L. Irvine one of the coinventors of this application in the February 1979 issue of the Journal of Water Pollution Control Federation Vol. 51, No. 2 starting on page 235 and continuing thru page 304. The SBR system has been found to be a particularly effective system for handling the treatment of chemical waste leachates using activated sludge and the activated sludges inoculated in accordance with our invention as will be described in more detail later.

The state-of-the-art for the "Microbial Removal of Hazardous Organic Compounds" is reviewed in an article so entitled by Hester Kobayashi and Bruce E. Rittmann in the March 1982 issue of Environmental Science Technology, Vol. 16, No. 3, pages 170A–183A. This publication lists a variety of microbial materials that have been published that can degrade, with quite varying ability, a number of organic compounds. Many of the microbial materials already known to metabolize halogenated organic wastes are capable of being employed in the process of our invention. We have found however, that by "acclimating" them, i.e. exposing the microbial materials for long periods to the recalcitrant organics so that generations upon generations are so exposed that they become adapted to survive in the mixed cultures of the ordinary municipal activated sludges that are used in accordance with our invention. The acclimated microbial materials will be exemplified in more detail later.

DESCRIPTION OF THE INVENTION

This invention contemplates using activated sludges that have been acclimated to metabolizing the recalcitrant obnoxious organics. In order to obtain such an acclimated activated sludge, it is necessary to use it to treat the chemical wastewater or leachate containing the recalcitrants. If the activated sludge happens to contain the strains of bacteria that will metabolize the recalcitrant organics, an acclimated sludge will result which may be employed in accordance with this invention. However, when the waste to be treated contains highly chlorinated organics and because of the absence in nature of large populations of bacteria that can biodegrade highly chlorinated organics, one should proceed in developing suitable strains using techniques such as disclosed in copending application Ser. No. 06/305077 filed Sept. 24, 1981 or in accordance with Chakrabarty's PAMB procedure. See the article by Kellogg, S. T.; Chatterjee, D. K. and Chakrabarty, A. M. in Science Vol. 214, Dec. 4, 1981 entitled "Plasmid-Assisted Molecular Breeding (PAMB)."

In order to maximize the advantages of this invention, it is important to make an analysis of the chemical waste to be treated to determine the composition of the contaminants, especially the recalcitrants, that are desired to be decomposed in the wastewater treatment process. Although the methods of this invention may be employed at the municipal wastewater treatment plant by inoculating the activated sludge with the acclimated microbial organisms that consume the chemical wastes going into the municipal sewer systems, the analysis for recalcitrants is more difficult because of the many unknowns being sewered into the conduits of the municipal system by the many industries being served by the system. For optimum results this invention contemplates that the chemical waste effluents at the chemical plant site be processed in accordance with this invention before they are put into the municipal system. In this manner, the composition of the effluents are known or can be more readily analyzed for the recalcitrants. Once having determined the indentity of recalcitrants to be decomposed, it becomes necessary to find microbial materials that will metabolize them, survive and preferably dominate the other microbes in the mixed culture of activated sludge.

In accordance with this invention from the soils or leachates of landfill sites that have stored the recalcitrant organics, microbial materials are isolated that have adapted to survive in said environment. The microbial materials should be cultured in accordance with the teachings of copending application Ser. No. 06/305079 (filed Sept. 14, 1981) or by other techniques to produce substantially pure cultures of the strains. If no landfill is found containing the recalcitrants then the process known as PAMB published by A. M. Chakrabarty referred to above may be use in an attempt to obtain strains that will survive and perhaps dominate in the activated sludges. Alternatively, and as information and collections of bacteria capable of metabolizing specific obnoxious organics are disclosed and made available such stains may be used as the starting material to make the innoculants.

Among the biological wastewater treatment systems which may be employed are the SBR system to be described in some detail. Other systems such as the continuous activated sludge, trickling filter, aerated lagoon, and anaerobic filter may also be adapted to more efficiently treat recalcitrant organics by the process and compositions of this invention.

A diagrammatic sketch of a Sequencing Batch Reactor (SBR) which is a new type of wastewater treatment system which we have found especially adapted for obtaining the improved results of this invention is given in the article by Robert L. Irvine referred to above.

The reactor is made of any material of construction generally employed in wastewater treatment facilities. It is usually cylindrical in shape and is equipped with a slow speed agitator or an air diffuser which are run at slow speeds. A peristaltic pump is installed in the inlet feed line to the reactor. The reactor is provided with an outlet and solenoid valves are provided at the outlet and in the air diffuser line. Programmable timers are provided at the pumps and the agitators if used or air diffusers and at the outlet line.

The SBR system may be composed of one or more such tanks and in biological waste treatment, each tank in the system has five basic operating modes and periods, each of which is named according to its primary function. The periods are fill, react, settle, draw and idle, in a time sequence. Fill (the receiving of raw waste) and draw (the discharge of treated effluent) must occur in each complete cycle for a given tank. React (the time to complete desired reactions), settle (the time to separate the organisms from the treated effluent), and idle (the time after discharging the tank and before refilling) can be eliminated depending on requirements of the treatment problem. For example, if an SBR system were being used for equalization only, each cycle might only involve fill and draw.

The time for a complete cycle is the total time between beginning of fill to end of idle in a single-tank system and between beginning of fill for the first reactor (arbitrarily defined) and the end or idle for the last reactor in a multiple-tank system. In a multiple-tank system, the reactors fill in sequence, the criterion being that one reactor must have completed draw prior to another completing fill.

Typical of the type of strains of bacteria that may be used as starting materials to make acclimated sludges or inoculants for treating leachates from landfills containing highly chlorinated organics and the organics they metabolize are given in the following Table 1. This table of information is given to illustrate the type of bacteria that may be employed and is not intended to limit the scope of our invention.

TABLE 1

| STRAINS OF INOCULANTS | | |
|---|---|---|
| Strain Designation | ATCC Number | Metabolizes |
| *Pseudomonas cepacia var., niagarous* | | |
| HCI (2CT) | ATCC-31945 | Chlorotoluenes, 2-Cl— |
| HCIV (3 CT) | ATCC-31941 | toluene, 3-Cl—toluene, 3, |
| HCV (2,4 DCB) | ATCC-31942 | 4-diCl—toluene, 2-6-diCl— |
| HCV (3,4 DCB) | ATCC-31940 | toluene, Benzoate, 4-Cl— |
| HCV (3,6 DCT)-2 | ATCC-31943 | benzoate, 2,4-diCl— |
| HCV (2,6 DCT)-3 | ATCC-31944 | benzoate, 2,4-D, 2,4-diCl— |
| HCV (3,4 DCT)-5 | ATCC-31939 | phenol, 2,4,5-T, Hexadecane |
| *Pseudomonas putida* | ATCC-39027 | 2,4,5-T (agent orange) |
| | ATCC-39028 | and related chlorinated |
| | ATCC-39029 | organics |
| | ATCC-39031 | |
| Norcardia | | Monochlorophenol, monochlorobenzoate |
| Achromobacter | | PCBs (mono- and dichlorobiphenyl |
| *Corynebacterium pyrogenes* | | Toxaphene |
| Chlosteridium sp. | | Lindane |
| Anacystis nidulans | | Dieldrin |
| Agmeneloum quardiplicatum | | Dieldrin |
| Clostridium | | DDT (1,1'-bis(p-chlorophenyl)-2,2,2-trichloroethane) |
| *Aspergillus niger* | | Pentachloronitrobenzene (PCNB) |
| Streptomyces sp. | | Methoxychlor |
| Micrococcus sp., | | Endrin |

The activated sludges that may be employed are not critical and any municipal or industrial sludge may be used since they generally contain a variety of organisms capable of metabolizing organics. Activated sludge is predominantly composed of bacteria, protoza and fungi. Other constituents are often present such as blue-green algae, rotifiers, insect lava, etc. but rarely in significant numbers.

The bacteria genera that may be present are given in the following Table II taken from a thesis by Karen L. Enderle, entitled Filamentous Organism Growth and Sequencing Batch Reactors submitted December 1980. Department of Civil Engineering—University of Notre Dame, South Bend, Ind. 46556. Over 300 different strains have been reported to exist in activated sludge.

The dominant bacteria in activated sludge are reported in said thesis and include the genera Achromobacter, Aerobacter, Alcaligenes, Bacillus, Bacterium, Escherichia, Flavobacterium, Klebsiella, Microbacterium, Norcardia, Paracolonbacterium, Pseudomonas and Zoogloea.

The protozoa are the next largest group in activated sludge and may be about 0.5% of the suspended solids in mixed liquor. About 230 species have been reported in activated sludge with ciliates constituting the dominant form.

The fungi found in activated sludge are the smallest group. Over 50 species from treatment plants in Europe and North America have been found including *Geotrichum canididum* and *Trichosproron*. The most common genera are Penicillum, Cephalosporium, Cladosporium and Alternaria. Yeasts such as Candida, Rhodotorula, Torulopsis and Trichlosporon were also found to be common in activated sludge.

Accordingly, the activated sludges which may be employed in our invention may be obtained from virtually any system since their compositions are so diversified and will contain more or less of at least some of the microbes required to metabolize some of the obnoxious organics in the wastes to be treated in accordance with our invention.

The sludges produced from the biological treatment of wastewaters can be disposed of by using them as soil conditioners if the sludge can be shown by chemical analysis to be free of any hazardous waste residues. Alternatively, the sludge can be placed in a secure landfill.

TABLE II

| Bacteria Genera Isolated from Activated Sludge (According to the Classification Structure in Bergeys' Manual) | |
|---|---|
| Bacteria/Genera | Morphology |
| PART II. GLIDING BACTERIA | |
| ORDER II. Cytophagales | |
| FAMILY I Cytophagacene | |
| GENUS II Flexibacter | rods of filaments (0.5 by 5–100 μm) |
| GENUS Microscilla | like Flexibacter only filaments occur in greater lengths |
| FAMILY II Begglatoaceae | |
| GENUS I Begglatos | cell in unattached filaments (1–30 by 4–20 μm) |
| GENUS II Vitreoscilla | unattached filaments (1.2–2 by 3–70 μm) |
| GENUS III Thiopioca | unattached filaments (variable length) common sheath |
| FAMILY IV Leucothrichaceae | |
| GENUS I Leucothrix | long, unbranched filaments (often >100 μm) diameter 3.5 μm |
| GENUS II Thiothrix | long, attached filaments |
| FAMILY Pelonometaceae | |
| GENUS Pelonema | unbranched, filaments (120 to 600 μm) |
| GENUS Acronema | unbranched, colorless filaments (120 μm) |
| *Incertae Hedis* | |
| GENUS Toxothrix | rods (0.5–0.75 by 3–6 μm) in filaments (400 μm) |
| PART III. SHEATHED BACTERIA | |
| GENUS Sphaerotilus | straight rods (0.7–2.4 by 3–10 μm) occurring in trichomes |
| GENUS Leptothrix | straight rods (0.6–1.5 by 3–12 μm) occurring in trichomes |
| GENUS Hallscomenobacter | thin rods (0.35–0.45 by 3.2–46 μm) in trichomes |
| GENUS Crenothrix | trichomes up to 1 cm. long |
| GENUS Clonothrix | trichomes up to 1.5 cm. long (attached or free) |
| GENUS Phagmidiothix | trichomes unbranched and attached (over 100 μm) |
| PART VI. SPIRAL AND CURVED BACTERIA | |

TABLE II-continued
Bacteria Genera Isolated from Activated Sludge (According to the Classification Structure in Bergeys' Manual)

| Bacteria/Genera | Morphology |
|---|---|
| FAMILY I Spirillaceae | |
| GENUS I Spirillum | Spirillum (0.2–0.8 μm by 0.5–5 μm) |
| PART VII. GRAM NEGATIVE RODS AND CODDI | |
| FAMILY I Pseudomonaceae | |
| GENUS I Pseudomonas | rods (0.5–1 to 1.5–4 μm) |
| GENUS III Zoogloeae | rods (0.5–1 by 1.0–3.0 μm) |
| FAMILY II. Azobacteraceae | |
| GENUS I Azobacter | Cocci singly, in pairs, or clumps-rarely > 4 cells |
| INCERTAE SEDIS | |
| GENUS Alcaligenes | Coccal rods (0.5–1.2 by 0.5–2.6 μm) |
| PART VIII. GRAM NEGATIVE FACULTATIVE | |
| ANAEROBIC RODS | |
| FAMILY ENTEROBACTERIACEAE | |
| GENUS I Escherichia | straight rods 1.1–1.5 by 2.0–6.0 μm) occurs singly or in pairs |
| GENUS IV Klebsiella | rods (0.3–1.5 μm by 0.6–6.0 μm) occurs singly, pairs or in short chains |
| INCERTAE SEDIS | |
| GENUS Chromobacterium | |
| GENUS Flavorbacterium | rods (0.6–1.2 by 1.5–6 μm) |
| PART XIV. GRAM-POSITIVE COCCI | |
| FAMILY I. MICROCOCEACEAE | |
| GENUS I. Micrococcus | cocci (0.5–3.5 μm) occurring singly, pairs, or clusters |
| GENUS II. Staphylococcus | cocci (0.5–1.5 μm) |
| FAMILY III. PEPTOCOCCACEAE | |
| GENUS IV. Sarcinn | cocci (1.8–3 μm) in packets |
| PART XV. ENDOSPORE FORMING RODS AND COCCI | |
| FAMILY I BACILLACEAE | |
| GENUS I Bacillus | rods (0.3–22 by 1.2–7.0 μm) in chains or singularly soil bacteria |
| PART XVII. ACTINOMYCETALES | |
| FAMILY II. MYCOBACTERIACEAE | |
| GENUS I. Mycobacterium | rods (0.2–0.6 μm) filamentous growth (fragment or disturbance) |
| FAMILY VI: NOCARDIACEAE | |
| GENUS I. Nocardia | branched filaments |
| FAMILY VII. STREPTOHYCETACEAE | |
| GENUS I. Streptomyces | slender, coenocytic hyphae (0.5–2.0 μm diameter) |
| FAMILY VIII. MICROMONOSPORACEAE | |
| GENUS I. Micromonospora | |
| INCERTAE SEDIS | |
| GENUS A. Brevibacterium | short rods |
| GENUS B. Microbacterium | short rods |
| CORYNEFORM GROUP OF BACTERIA | |
| GENUS I. Corynebacterium | rods in palisade arrangement |
| GENUS II. Arthrobacter | spherical-angular cells |

EXAMPLES OF THE INVENTION

The following examples are given to further describe our invention, however, they are given for illustrative purposes only and are not intended to limit the scope of our invention except as defined in the appended claims.

EXAMPLE I

Raw Landfill Leachate Preparation

Sufficient raw landfill leachate from a chemical landfill site in Niagara Falls, N.Y. that has been used for obnoxious organic wastes including chlorinated organics for a period of over twenty years, was taken from the supply to feed the SBR reactors (previously described) for each day. The pH of the raw leachate was measured to be 4.3 and surprisingly it was determined that a viable population of *Pseudomonas cepacia*, var., *niagarous* was present. The sample was diluted, as necessary, and the pH was adjusted from 4.3 to 7.5 using NaOH solution. One very high-strength leachate supply was further treated following pH adjustment by aeration 30 minutes. After aeration was completed, the raw landfill leachate was first filtered through a Whatman number 1 paper filter, then through a Millipore Microfiber glass filter. After filtration, the pH is rechecked and adjusted to 7.5 if necessary. The pretreated but undiluted landfill leachate was typically characterized by the following analysis.

| | |
|---|---|
| Total Organic Carbon (TOC), mg/l | 3000 |
| Chemical Oxygen Demand (COD), mg/l | 9200 |
| pH | 7.5 |
| Orthophosphate, mg/l as Phosphorous (P) | 0 |
| Total Phosphate, mg/l as P | 92 |
| Ammonia Nitrogen, mg/l as Nitrogen (N) | 130 |
| Nitrate plus Nitrite Nitrogen, mg/l as N | 50 |
| Suspended Solids, mg/l | 220 |
| Volatile Suspended Solids, mg/l | 140 |
| Total Dissolved Solids, g/l | 22.4 |

EXAMPLE II

The SBR Reactor Startup and Stabilization

Three 15 liter glass reactors (battery jars) 23 cm diameter and 28 cm in height were set up as SBR reactors as previously described. Agitation was supplied by diffused air and/or a mechanical mixer rotating at 12 revolutions per minute. Peristaltic pumps were used to feed the pretreated landfill leachate to the reactors and draw off the treated effluent. A solenoid valve was used to control the diffused air supply. Overall system operation was controlled by the use of programmable timers.

Nine liters was used as a maximum liquid volume; air was supplied through diffuser stones at relatively high rates such as 8 to 10 cfh which is typical for most laboratory SBR reactors. Substantial spattering and evaporation can occur and this was minimized by using glass plates to cover the reactors.

The reactors were started with mixed liquor suspended solids (MLSS) obtained from a sewage treatment plant located at Culver City, Ind. and one inoculation of *Psuedomonas cepacia* var., *niagarous*. The operating policy was as follows:

| |
|---|
| 10 Hours Fill - with Aeration |
| 10 Hours React - with Aeration |
| 1 Hour Settle |
| 1 Hour Draw |
| 24 Hour/Day Cycle |

The reactors were operated for about six months. The following chart summarizes the typical reactor characteristics during this period.

| Reactor | MLSS mg/l | MLVSS[1] mg/l | MLVSS[1] % | $RO_2$[2] mg/l Per Hour Unspiked | $RO_2$[2] mg/l Per Hour Spiked | TOC[3] Feed/Effluent mg/l | pH |
|---|---|---|---|---|---|---|---|
| A | 2,900 | 1,450 | 50 | 5 | 17 | 900/90 | 7.5 |

[1]Mixed liquor volatile suspended solids.
[2]Oxygen ulilization rate.
[3]Total Organic Carbon.

The contents of Reactor A, about 9 liters, was combined and mixed with mixed liquor from the sewage treatment plant identified above to a total of 24 liters. Eight liters were placed in each of two reactors and designated A and B. The operating cycles for each reactor were as given in the following chart.

| Reactor Designation | Operating Cycle and Primary Purpose |
|---|---|
| A | 3 h aerated FILL, 20 h aerated REACT, 1 h SETTLE and about 5 min. DECANT. |
| B | Operated as Reactor A, except for inoculation of the specially prepared microbial culture. |

EXAMPLE III

Preparation of Microbial Culture for Inoculation

The special culture media was prepared according to two different specifications (a) and (b) as follows:

| (a) Tryptone Nutrient Agar (TNA) | |
|---|---|
| Tryptone | 2.5 g |
| Yeast Extract | 1.25 g |
| Dextrose | 0.5 g |
| Sodium Chloride, NaCl | 4.25 g |
| Granular Agar | 10.0 g |
| Calcium Chloride, $CaCl_2$, Solution (1.5%) | 5.0 ml |
| Distilled Water | 500 ml |

| (b) Tryptone Nutrient Broth (TNB) | |
|---|---|
| Tryptone | 2.5 g |
| Yeast Extract | 1.25 g |
| Dextrose | 0.5 g |
| Sodium Chloride, NaCl | 4.25 g |
| Potassium Nitrate, $KNO_3$ | 2.0 g |
| Distilled Water | 500 ml |

The TNA was autoclaved, poured into petri dishes, and stored at 4° C. Using aseptic techniques, one loop of bacteria was transferred from the stock slant of bacterial strain HCV 2,6(DT)-2 deposited with the American Type Culture Collection, Rockville, Md. and designated ATCC #31943 and streaked on the TNA plate, and then incubated at 35° C. The 500-ml batches of TNB were prepared as needed. Following autoclaving and cooling, a loop of bacteria from the TNA was aseptically inoculated into the TNB and placed on a shaker at room temperature for two days. This proved the source of specially prepared organisms when needed.

EXAMPLE IV

Inoculation of Reactor B with Prepared Culture

Reactors A and B were fed with 590 ml of pretreated landfill leachate (pretreatment procedure described above) with no MLSS wasting since daily wasting of MLSS resulted in excess loss of this material. The difference between volume fed and draw is due to evaporation. 500 ml of TNB broth containing strain HCV 2,6(DCT)-2 (ATCC #31943) was added to Reactor B at three-day intervals over a 12-day period.

Tables III and IV summarize the performance characteristics of each reactor over the time period when Reactor B was inoculated. Table V summarizes the effluent analytical results of reactors A and B. Table VI summarizes the overall reactor performances and the effluent quality from each reactor. Reactor B which was inoculated with HCV 2,6(DCT)-2 clearly showed significant improvement over reactor A in TOC removal and suspended and volatile solids removal. The fourfold increase in oxygen uptake rates ($RO_2$mg/l/hr.) further demonstrates the rapid metabolism of the obnoxious chemicals by the inoculated Reactor B.

Thus in accordance with this invention, we have provided processes and compositions which can be used to treat chemical waste landfill leachates to significantly reduce the concentration of the obnoxious wastes. The TOC (total organic carbon) content is reduced by 95% and the TOX (total organic halogen) content is reduced by 50% as can be seen from the summary of results showing the reduction in TOX and TOC given in the following chart.

| Reactor | TOC mg/l | TOX mg/l |
|---|---|---|
| Feed | 3000 | 200 |
| A | 225 | 100 |
| B | 93 | 80 |

TABLE III

PERFORMANCE CHARACTERISTICS - REACTOR A

| Date | MLSS mg/l | MLVSS mg/l | MLVSS % | $RO_2$ mg/l Per Hour Unspiked | $RO_2$ mg/l Per Hour Spiked | TOC mg/l Feed | TOC mg/l Effluent | pH | Volume in ml Feed | Volume in ml Draw | MLSS Wastes |
|---|---|---|---|---|---|---|---|---|---|---|---|
| January 21 | 3930 | 2120 | 54 | | | | | 7.8 | 0 | 0 | 0 |
| 22 | | | | | | | 1000 | | | 0 | 0 |

TABLE III-continued
PERFORMANCE CHARACTERISTICS - REACTOR A

| Date | MLSS mg/l | MLVSS mg/l | MLVSS % | RO₂ mg/l Per Hour Unspiked | RO₂ mg/l Per Hour Spiked | TOC mg/l Feed | TOC mg/l Effluent | pH | Volume in ml Feed | Volume in ml Draw | Volume in ml MLSS Wastes |
|---|---|---|---|---|---|---|---|---|---|---|---|
| 23 | | | | | | | | | 1000 | 700 | 200 |
| 24 | | | | | | | | | 1000 | 400 | 200 |
| 25 | | | | | | | | | 1000 | 850 | 200 |
| 26 | | | | | | | | | 1000 | 1000 | 200 |
| 27 | | | | | | | | | 1000 | 900 | 200 |
| 28 | | | | | | 500 | 110 | 7.7 | 1000 | 800 | 200 |
| 29 | | | | | | | | | 1000 | 750 | 200 |
| 30 | | | | | | | | | 1000 | 700 | 200 |
| 31 | 1650 | 870 | 53 | 3 | 26 | 550 | 90 | 7.5 | 1000 | 850 | 200 |
| February 1 | | | | | | | | | 1000 | 800 | 200 |
| 2 | | | | | | | | | 1000 | 800 | 200 |
| 3 | 1250 | 680 | 54 | | | | | | 300 | 200 | 0 |
| 4 | 1270 | 680 | 53 | | | | | 8.0 | 300 | 200 | 0 |
| 5 | 1580 | 860 | 54 | 5 | 53 | 3200 | 120 | 8.2 | 590 | 400 | 0 |
| 6 | 1390 | 800 | 57 | | | 3200 | 110 | 8.2 | 590 | 400 | 0 |
| 7 | | | | | | | | 7.7 | 590 | 400 | 0 |
| 8 | 1580 | 940 | 59 | | | 3000 | 180 | 7.5 | 590 | 400 | 0 |
| 9 | 1870 | 1140 | 61 | | | | | | 590 | 400 | 0 |
| 10 | | | | | | | | 7.6 | 590 | 400 | 0 |
| 11 | 2090 | 1250 | 60 | 9 | 17 | 3000 | 280 | 7.5 | 590 | 400 | 0 |
| 12 | | | | | | | | 7.7 | 590 | 400 | 0 |
| 13 | 1780 | 1040 | 58 | | | 3000 | 350 | 7.6 | 590 | 400 | 0 |
| 14 | | | | 9 | 15 | | | 7.5 | 590 | 400 | 0 |
| 15 | | | | | | | | 7.5 | 590 | 400 | 0 |
| 16 | | | | | | | | 7.5 | 590 | 400 | 0 |
| 17 | | | | | | | | 7.4 | 590 | 400 | 0 |
| 18 | 1600 | 960 | 60 | 6 | 14 | 3200 | 400 | 7.7 | 590 | 400 | 0 |
| 19 | | | | | | | | 7.7 | 590 | 400 | 0 |
| 20 | | | | | | | | 7.6 | 590 | 400 | 0 |
| 21 | 3270 | 1800 | 55 | 21 | 93 | 3200 | 310 | 7.6 | 590 | 400 | 0 |
| 22 | | | | | | | | 7.7 | 300 | 200 | 0 |
| 23 | | | | | | | | 7.7 | 300 | 200 | 0 |
| 24 | 2810 | 1580 | 56 | 11 | 165 | 3100 | 140 | 7.8 | 0 | 0 | 0 |
| 25 | | | | | | | | 7.9 | 0 | 0 | 0 |
| 26 | | | | | | | | 7.8 | 590 | 0 | 0 |
| 27 | 2840 | 1550 | 55 | 8 | 87 | 3000 | 140 | 7.6 | 590 | 400 | 0 |
| 28 | | | | | | | | 7.8 | 590 | 400 | 0 |

TABLE IV
PERFORMANCE CHARACTERISTICS - REACTOR B

| Date | MLSS mg/l | MLVSS mg/l | MLVSS % | RO₂ mg/l Per Hour Unspiked | RO₂ mg/l Per Hour Spiked | TOC mg/l Feed | TOC mg/l Effluent | pH | Volume in ml Feed | Volume in ml Draw | Volume in ml MLSS Wastes |
|---|---|---|---|---|---|---|---|---|---|---|---|
| January 21 | 3750 | 2020 | 54 | | | | | 7.8 | 0 | 0 | 0 |
| 22 | | | | | | | | | 1000 | 0 | 0 |
| 23 | | | | | | | | | 1000 | 800 | 200 |
| 24 | | | | | | | | | 1000 | 850 | 200 |
| 25 | | | | | | | | | 1000 | 600 | 200 |
| 26 | | | | | | | | | 1000 | 900 | 200 |
| 27 | | | | | | | | | 1000 | 850 | 200 |
| 28 | | | | | | 500 | 100 | 7.8 | 1000 | 750 | 200 |
| 29 | | | | | | | | | 1000 | 750 | 200 |
| 30 | | | | | | | | | 1000 | 700 | 200 |
| 31 | 1670 | 940 | 56 | 3 | 23 | 550 | 70 | 7.4 | 1000 | 950 | 200 |
| February 1 | | | | | | | | | 1000 | 850 | 200 |
| 2 | | | | | | | | | 1000 | 800 | 200 |
| 3 | 900 | 510 | 57 | | | | | | 300 | 200 | 0 |
| 4 | 910 | 500 | 55 | | | | | 8.0 | 300 | 200 | 0 |
| 5 | 1440 | 790 | 55 | 5 | 60 | 3200 | 110 | 8.2 | 590 | 400 | 0 |
| 6 | 1440 | 800 | 56 | | | 3200 | 130 | 8.2 | 590 | 400 | 0 |
| 7 | | | | | | | | 7.7 | 590 | 400 | 0 |
| 8 | 2250 | 1300 | 58 | | | 3000 | 120 | 7.7 | 590 | 400 | 0 |
| 9 | 2230 | 1320 | 59 | | | | | | 590 | 400 | 0 |
| 10 | | | | | | | | 7.7 | 590 | 400 | 0 |
| 11 | 2860 | 1680 | 59 | 15 | 174 | 3000 | 100 | 7.6 | 590 | 400 | 0 |
| 12 | | | | | | | | 7.4 | 590 | 400 | 0 |
| 13 | 3200 | 1870 | 58 | | | 3000 | 80 | 7.6 | 590 | 400 | 0 |
| 14 | | | | 20 | 300 | 3000 | 80 | 7.6 | 590 | 400 | 0 |
| 15 | | | | | | | | 7.8 | 590 | 400 | 0 |
| 16 | | | | | | | | 7.6 | 590 | 400 | 0 |
| 17 | | | | | | | | 7.5 | 590 | 400 | 0 |
| 18 | 4190 | 2490 | 59 | 14 | 492 | 3200 | 90 | 7.8 | 590 | 400 | 0 |
| 19 | | | | | | | | 7.8 | 590 | 400 | 0 |
| 20 | | | | | | | | 8.0 | 590 | 400 | 0 |

TABLE IV-continued

PERFORMANCE CHARACTERISTICS - REACTOR B

| Date | MLSS mg/l | MLVSS mg/l | MLVSS % | RO₂ mg/l Per Hour Unspiked | RO₂ mg/l Per Hour Spiked | TOC mg/l Feed | TOC mg/l Effluent | pH | Volume in ml Feed | Volume in ml Draw | MLSS Wastes |
|---|---|---|---|---|---|---|---|---|---|---|---|
| 21 | 4820 | 2780 | 58 | 12 | 430 | 3200 | 110 | 7.9 | 590 | 400 | 0 |
| 22 | | | | | | | | 8.0 | 300 | 200 | 0 |
| 23 | | | | | | | | 7.9 | 300 | 200 | 0 |
| 24 | 4150 | 2440 | 59 | 9 | 470 | 3100 | 100 | 8.0 | 0 | 0 | 0 |
| 25 | | | | | | | | 7.9 | 0 | 0 | 0 |
| 26 | | | | | | | | 7.9 | 590 | 0 | 0 |
| 27 | 4630 | 2690 | 58 | 11 | 107 | 3000 | 120 | 7.7 | 590 | 400 | 0 |
| 28 | | | | | | | | 7.6 | 590 | 400 | 0 |

TABLE V

EFFLUENT ANALYTICAL RESULTS

| Date | ORTHO-P mg/l | NH₃—N mg/l | NO_x mg/l | EFF. SS mg/l | VSS mg/l | % |
|---|---|---|---|---|---|---|
| Reactor A | | | | | | |
| January 28 | 0.2 | 4.0 | 5.0 | 100 | | |
| 31 | 0.2 | 1.8 | | | | |
| February 5 | 0.1 | 2.0 | | | | |
| 11 | | | | 200 | | |
| 13 | 0.0 | 7.0 | 2.0 | 220 | 100 | 45 |
| Reactor B | | | | | | |
| January 28 | 0.1 | 3.5 | 5.0 | 190 | | |
| 31 | 1.1 | 3.5 | | | | |
| February 5 | 0.1 | 1.5 | | | | |
| 11 | | | | 90 | | |
| 13 | 0.04 | 4.0 | 3.5 | 90 | 50 | 56 |

TABLE VI

SUMMARY OF OVERALL REACTOR PERFORMANCE AND EFFLUENT QUALITY

| Reactor | MLSS Initial | MLSS Final | RO₂ mg/l Per Hour Unspiked | RO₂ mg/l Per Hour Spiked | Feed TOC | Effluent TOC | Effluent SS | Effluent VSS |
|---|---|---|---|---|---|---|---|---|
| A | 1200 | 2800 | 12 | 63 | 3000 | 225 | 210 | 100 |
| B | 900 | 4600 | 12 | 290 | 3000 | 94 | 90 | 50 |

Although our invention has been described using specific examples and certain preferred embodiments thereof, we do not intend that our invention be limited in scope except as expressly defined in the appended claims.

We claim:

1. A microbial culture system comprising activated sludge and a supplemental microbial inoculant selected from the group consisting of ATCC 31945, ATCC 31941, ATCC 31942, ATCC 31940, ATCC 31943, ATCC 31944, ATCC 31939, and mutants thereof, which is acclimated to metabolize chemical wastewaters and chemical waste landfill leachates, containing halogenated organic compounds.

2. A microbial culture system according to claim 1 wherein the inoculant is ATCC 31945.

3. A microbial culture system according to claim 1 wherein the inoculant is ATCC 31941.

4. A microbial culture system according to claim 1 wherein the inoculant is ATCC 31942.

5. A microbial culture system according to claim 1 wherein the inoculant is ATCC 31940.

6. A microbial culture system according to claim 1 wherein the inoculant is ATCC 31943.

7. A microbial culture system according to claim 1 wherein the inoculant is ATCC 31944.

8. A microbial culture system according to claim 1 wherein the inoculant is ATCC 31939.

9. The process for reducing the amount of obnoxious halogenated organic compounds in chemical process wastewaters and chemical landfill leachates which comprises treating the wastewaters or leachates with an activated sludge containing bacteria selected from the group consisting of ATCC 31945, ATCC 31941, ATCC 31942, ATCC 31940, ATCC 31943, ATCC 31944, ATCC 31939 and mutants thereof capable of metabolizing the obnoxious halogenated organic compounds in a biological wastewater system.

10. The process of claim 9 wherein the biological wastewater system is a Sequencing Batch Reactor.

11. The process of claim 10 wherein the activated sludge is inoculated with a bacteria that have been continuously exposed to the obnoxious halogenated organic compounds in established landfills containing said materials.

12. The process of claim 9 wherein the biological wastewater system is a Continuous Flow System.

13. The method of treating chemical process wastewaters and chemical waste landfill leachates to biodegrade the recalcitrant organic compounds contained therein, which comprises:

1. Analyzing the chemical waste to determine the composition of the contaminants to be removed,
2. Preparing a pure culture of a microbial organism capable of metabolizing the recalcitrant contaminants, selected from the group consisting of ATCC 31945, ATCC 31941, ATCC 31942, ATCC 31940, ATCC 31943, ATCC 31944, ATCC 31939, and mutants there of,
3. Inoculating a biologically active waste treatment culture capable of metabolizing the non-recalcitrant components of the chemical wastewater or leachate with the prepared culture of the microorganisms obtained by Step 2,
4. Employing the organism system obtained by Step 3 in a biological wastewater facility to biodegrade the recalcitrant and non-recalcitrant chemical components of the chemical process wastewater or leachate,
5. Disposing of the waste effluent and waste sludge produced.

14. The method of claim 13 wherein the waste to be treated is chemical landfill leachate containing recalcitrant organic and halogenated organic compounds and wherein the inoculant is prepared from bacteria obtained from the location of the landfill or leachate.

15. The method of claim 14 wherein the leachate contains chlorinated aromatic compounds and the inoculant contains *Pseudomonas cepacia* var., nigarous selected from the group consisting of ATCC 31945, ATCC 31941, ATCC 31942, ATCC 31940, ATCC 31943, ATCC 31944, ATCC 31939 and mutants thereof.

16. The process of claim 15 wherein the inoculant is prepared from a leachate having an acid pH less than 7.

* * * * *